(12) United States Patent
Zhu et al.

(10) Patent No.: US 11,119,084 B2
(45) Date of Patent: *Sep. 14, 2021

(54) METHODS AND DEVICES FOR DETECTING MERCURY ISOTOPES IN NATURAL GAS

(71) Applicant: PetroChina Company Limited, Beijing (CN)

(72) Inventors: Guangyou Zhu, Beijing (CN); Shunlin Tang, Beijing (CN)

(73) Assignee: PetroChina Company Limited, Beijing (CN)

( * ) Notice: Subject to any disclaimer, the term of this patent is extended or adjusted under 35 U.S.C. 154(b) by 298 days.

This patent is subject to a terminal disclaimer.

(21) Appl. No.: 16/389,084

(22) Filed: Apr. 19, 2019

(65) Prior Publication Data

US 2020/0132648 A1 Apr. 30, 2020

(30) Foreign Application Priority Data

Oct. 31, 2018 (CN) .......................... 201811284109.7

(51) Int. Cl.
| | |
|---|---|
| *G01N 33/28* | (2006.01) |
| *G01N 33/22* | (2006.01) |
| *G01N 33/00* | (2006.01) |
| *G01N 21/64* | (2006.01) |
| *G01N 27/02* | (2006.01) |
| *H01J 49/02* | (2006.01) |

(52) U.S. Cl.
CPC ..... *G01N 33/0045* (2013.01); *G01N 21/6404* (2013.01); *G01N 27/025* (2013.01);
(Continued)

(58) Field of Classification Search
CPC .. G01N 27/025; G01N 33/0045; G01N 33/22; G01N 33/225; G01N 33/2835;
(Continued)

(56) References Cited

U.S. PATENT DOCUMENTS

| | | |
|---|---|---|
| 3,933,431 A | 1/1976 | Trujillo et al. |
| 4,758,519 A | 7/1988 | Nakao et al. |
| (Continued) | | |

FOREIGN PATENT DOCUMENTS

| | | |
|---|---|---|
| AU | 2019202485 | 5/2020 |
| CN | 2684180 Y | 3/2005 |
| (Continued) | | |

OTHER PUBLICATIONS

Zheng et al. Journal of Analytical Atomic Spectrometry, vol. 22, Jul. 30, 2007, pp. 1097-1104.*

(Continued)

*Primary Examiner* — Maureen Wallenhorst
(74) *Attorney, Agent, or Firm* — Foley & Lardner LLP (57) ABSTRACT

The invention provides a method and device for measuring mercury isotopes in natural gas. The method includes the following steps: (1) primary enrichment: subjecting natural gas to a three-stage cascading absorption with an acidic potassium permanganate aqueous solution, and collecting all of the acidic potassium permanganate aqueous solutions in which natural gas is absorbed in step (1); (2) mercury purification and enrichment: reducing the mercury absorbed in the step (1) to mercury vapor with a stannous chloride solution, and then purifying and enriching the mercury vapor by using an acidic potassium permanganate aqueous solution; (3) detecting the acidic potassium permanganate solution in which the mercury vapor is enriched in step (2) to determine the total mercury content therein; and (4) detecting the acidic potassium permanganate solution in which the mercury vapor is enriched in step (2) to determine the composition/content of stable mercury isotopes therein.

17 Claims, 1 Drawing Sheet

(52) U.S. Cl.
CPC ....... *G01N 33/225* (2013.01); *G01N 33/2835* (2013.01); *H01J 49/025* (2013.01)

(58) Field of Classification Search
CPC ... G01N 33/20; G01N 21/6404; H01J 49/025; Y10T 436/24; Y10T 436/25; Y10T 436/25375; Y10T 436/255
USPC .. 436/60, 73, 77, 79, 81, 84, 164, 172, 173, 436/174, 177, 178, 181; 422/82.05, 422/82.08, 527, 88
See application file for complete search history.

(56) References Cited

U.S. PATENT DOCUMENTS

| | | | |
|---|---|---|---|
| 5,733,786 A * | 3/1998 | Green | G01N 31/22 422/504 |
| 6,197,269 B1 | 3/2001 | Jansen et al. | |
| 7,144,736 B2 * | 12/2006 | Noda | G01N 1/2247 436/81 |
| 8,992,769 B2 * | 3/2015 | O'Rear | C10G 29/02 208/251 R |
| 9,125,596 B2 | 9/2015 | Leclerc et al. | |
| 9,574,140 B2 * | 2/2017 | Lord, III | G01N 33/2858 |
| 9,712,035 B1 | 7/2017 | Bango et al. | |
| 9,988,584 B2 | 6/2018 | Oehr | |
| 10,816,532 B2 * | 10/2020 | Zhu | G01N 21/3103 |
| 2002/0033097 A1 | 3/2002 | El-Shoubary et al. | |
| 2004/0237634 A1 * | 12/2004 | Makino | B01D 53/8665 73/61.52 |
| 2006/0021506 A1 | 2/2006 | Hakka et al. | |
| 2009/0004644 A1 | 1/2009 | Kiel et al. | |
| 2009/0169450 A1 | 7/2009 | Naito et al. | |
| 2010/0126909 A1 | 5/2010 | Bhasin et al. | |
| 2012/0067786 A1 | 3/2012 | Gallup et al. | |
| 2012/0205533 A1 | 8/2012 | Ariya et al. | |
| 2013/0281553 A1 | 10/2013 | Kubic et al. | |
| 2013/0306311 A1 | 11/2013 | Cooper et al. | |
| 2014/0262955 A1 | 9/2014 | Cooper et al. | |
| 2015/0047465 A1 | 2/2015 | Langley | |
| 2015/0050344 A1 | 2/2015 | Watson et al. | |
| 2015/0108040 A1 | 4/2015 | Lord et al. | |
| 2015/0218462 A1 | 8/2015 | Lord et al. | |
| 2016/0003023 A1 | 1/2016 | O'Rear et al. | |
| 2016/0045841 A1 | 2/2016 | Kaplan et al. | |
| 2016/0122658 A1 | 5/2016 | O'Rear et al. | |
| 2016/0332108 A1 | 11/2016 | O'Rear et al. | |
| 2018/0340174 A1 | 11/2018 | Lundorf et al. | |
| 2019/0275464 A1 | 9/2019 | Mazyck et al. | |
| 2020/0132648 A1 | 4/2020 | Zhu et al. | |

FOREIGN PATENT DOCUMENTS

| | | |
|---|---|---|
| CN | 101349639 A | 1/2009 |
| CN | 201529482 U | 7/2010 |
| CN | 201662528 U | 12/2010 |
| CN | 201740738 U | 2/2011 |
| CN | 102608271 A | 7/2012 |
| CN | 202533285 U | 11/2012 |
| CN | 103076215 A | 5/2013 |
| CN | 103149057 A | 6/2013 |
| CN | 103293326 A | 9/2013 |
| CN | 103894116 A | 7/2014 |
| CN | 104122123 A | 10/2014 |
| CN | 104297174 A | 1/2015 |
| CN | 104436994 A | 3/2015 |
| CN | 204346807 U | 5/2015 |
| CN | 105699160 A | 6/2016 |
| CN | 206411013 U | 8/2017 |
| CN | 107389387 A | 11/2017 |
| CN | 206945380 U | 1/2018 |
| CN | 107817236 | 3/2018 |
| CN | 107941718 A | 4/2018 |
| CN | 108020601 A | 5/2018 |
| CN | 207585997 U | 7/2018 |
| CN | 108956238 | * 12/2018 |
| CN | 108956238 A | 12/2018 |
| CN | 109142017 | * 1/2019 |
| JP | H06-265531 A | 9/1994 |
| JP | 2003-240687 A | 8/2003 |
| JP | 2016-070726 A | 5/2016 |
| WO | WO-2016/108766 A1 | 7/2016 |

OTHER PUBLICATIONS

Brombach et al. Talanta, vol. 199, Feb. 20, 2019, pp. 277-284.*
Canadian First Office Action and Search Report, App. No. 3039564, PetroChina Company Limited, 6 pages (dated Jul. 27, 2020).
Notice of Allowance for U.S. Appl. No. 16/389,481, 7 pages (dated Aug. 3, 2020).
Australian First Examination Report, App. No. 2019202479, PetroChina Company Limited, 6 pages (dated Nov. 20, 2019).
Australian First Examination Report, App. No. 2019202485, PetroChina Company Limited, 6 pages (dated Nov. 29, 2019).
Brahma, N., "The on line determination of mercury in process streams using atomic spectrometry," Ph.D. Thesis, University of Plymouth (Plymouth, United Kingdom), 249 pages (Nov. 2000).
Hoffart et al., "A two-step acid mercury removal process for pulverized coal," Fuel, vol. 85. pp. 1166-1173 (2006).
Lopez-Anton et al., "Analytical methods for mercury analysis in coal and coal combustion by-products," Int'l Journal of Coal Geology, 94, 47 pages (2012).
Smith, C., "Isotopic geochemistry of mercury in active and fossil hydrothermal systems," Ph.D. Thesis, University of Michigan (Ann Arbor, Michigan), 174 pages (2010).
First Office Action for CN App. No. 201811284109.7 dated Sep. 3, 2020 (26 pages).
Huang et al., "A Combustion-Trapping Pretreatment Technique for Environmental Samples and Its Application in Mercury Isotopic Analysis", Fenxi Ceshi Xuebao (Journal of Instrumental Analysis), vol. 35, No. 6, Jun. 2016, pp. 704-708 (5 pages).
Li et al., "Volatility and Speculation of Mercury during Pyrolysis and Gasification of Five Chinese coals", Energy Fuels, vol. 25, No. 9, Jul. 11, 2012, pp. 3988-3996 (9 pages).
Search Report for CN Appn. No. 201811284109.7 dated Aug. 28, 2020 (9 pages).
Sheng et al., "Prevention of mercury damage", Petrochemical Industry Press, Jan. 1978, pp. 78-79 (6 pages).
Wang et al., "Effect of coordinated Air Pollution Control Devices in Coal-Fired Power Plants on Arsenic Emissions", Energy Fuels, vol. 31, No. 7, Jun. 2017 (39 pages).
Wang, Lina, "Mercury speciation and isotopic composition in flue gas from Coal-fired Power Plants in Inner Mongolia", China Excellent Master's Thesis Full-text Database: Engineering Science and Technology Series I, Dec. 15, 2017 (130 pages).
English-language Abstract of Chen, Gengliang, "Standardization of Mercury Determination in Natural Gas," Petroleum Planning & Engineering, vol. 8, No. 1, 4 pages (Jan. 1997).
English-language Abstract of Deng et al., "Analysis on Mercury Forms in Oil and Gas," Oil and Gas Treating and Processing, vol. 31, No. 5, 5 pages (Oct. 2013).
English-language Abstract of Duan et al., "Experimental Study on Mercury Release and Adsorption During Coal Pyrolysis," PTCA Journal of Taiyuan University of Technology, vol. 41, No. 5, 3 pages (Sep. 2010).
English-language Abstract of Leng et al., "Discussion on Analysis Method of Trace Mercury in Liquefied Natural Gas," Guangzhou Chemical Industry, vol. 42, No. 23, 3 pages (Dec. 2014).
English-language Abstract of Li, "Determination of Mercury in Crude Oil by Cold Atomic Absorption Spectrometry," Chinese Journal of Spectroscopy Laboratory, vol. 21, No. 4, 3 pages (Jul. 2004).
English-language Abstract of Liu et al., "Advance of Research on Mercury and its Compounds Collecting and Measuring Methods," Natural Gas Geoscience, vol. 17, No. 4, 7 pages (Aug. 2006).

(56) References Cited

OTHER PUBLICATIONS

English-language Abstract of Tu, "Preliminary Study on Mercury Occurrence in Source Rocks," ACTA Sedimentolgica Sinica, vol. 3, No. 1, 7 pages (Jan. 1985).
English-language Abstract of Wang et al., "AFS Determination of Pb, As, and Hg in Crude Oil with Microwave Assisted Sample Digestion," PTCA (Part B: Chem. Anal.), vol. 48, No. 9, 3 pages (2012).
English-language Abstract of Wei et al., "An Introduction to XG-7Z Zeeman Mercury Measurement Instrument and the Analytical Method for Trace Concentrations of Mercury," Geophysical &Geochemical Exploration, vol. 38, No. 2, 8 pages (Apr. 2014).
English-language Abstract of Xue, "Research Progress on Analytical Methods of Mercury in Petroleum," Petroleum and Petrochemical Today, vol. 16, No. 6, 4 pages (Jun. 2008).
English-language translation of National Environmental Protection Standard of the People's Republic (HJ 543-2009): Stationary source emission-determiniation of mercury—cold atomic absorption spectrophotometry, 4 pages (Dec. 30, 2009).
English-language translation of National Standard of the People's Republic (GB/T 16157-1996): The determination of particulates and sampling methods of gaseous pollutants emitted from exhaust gas of stationary source, 4 pages (Mar. 6, 1996).
English-language translation of Paragraph 5, p. 10 of Xinliang, Zhao, "Experimental Study on the Transformation of Mercury Element During Coal Pyrolysis Gasification," Huazhong University of Science and Technology Master's Thesis, 3 pages (Jan. 2012).
Australian First Examination Report, App. No. 2019202470, PetroChina Company Limited, 5 pages (dated Apr. 16, 2020).

\* cited by examiner

METHODS AND DEVICES FOR DETECTING MERCURY ISOTOPES IN NATURAL GAS

CROSS-REFERENCE TO RELATED PATENT APPLICATIONS

This application claims the benefit of Chinese Patent Application No. 201811284109.7, filed Oct. 31, 2018, which is incorporated herein by reference in its entirety.

TECHNICAL FIELD

The present invention relates to a field of natural gas exploitation. In particular, the present invention relates to a method and device for measuring mercury isotopes in natural gas.

BACKGROUND

As an identification index for natural gas genesis, mercury vapor content in natural gas is proposed as early as 1974 by a scientist, H. A. озроьа, in former Soviet Union after studying various oil and gas fields. It is very common for oils and natural gases to contain mercury in a relative higher mercury content, which is usually higher than the atmospheric mercury content (with background value of mercury in atmosphere of 1.5 to 2.0 $ng/m^3$) by two or even more orders of magnitude. The coal-type gas generally has a higher mercury content than that in oil-type gas, however, there is an overlapped range therebetween, which makes it impossible to accurately identify the gas type by mercury vapor contents. This problem may be expected to be solved by the accurate mercury isotope information. Currently, there are two kinds of methods to collect mercury in natural gas, a mercury oxide method and an amalgam method. The mercury oxide method, in turn, can be divided into a liquid oxidation method and a solid oxidation method. In the liquid oxidation method, natural gas is firstly passed through an absorption bottle containing potassium permanganate, nitric acid or reverse aqua regia, in which agents the mercury in the natural gas is absorbed, then the absorption liquid is recovered and transported back to the laboratory, after that the divalent mercury ion in the absorption liquid is reduced by stannous chloride to mercury vapor, which is trapped by a mercury-trapping gold tube with high-purity nitrogen gas as a carrier gas, and then is measured by a mercury detector. In the solid oxidation method, natural gas is passed through a tube containing an iodine silica gel or an activated carbon to absorb mercury in natural gas, which is transported back to the laboratory and subjected to pyrolysis to release mercury into a mercury-trapping gold tube, and then is measured by a mercury detector for the mercury content analysis. In the amalgam method, natural gas is passed through a quartz tube containing gold/platinum wires, silver chips or gold-plated quartz sand or the like to form an amalgam so that the mercury is enriched. The sampling method for detecting the mercury content in natural gas employed as a National Standard is a sampling method by iodine chemisorption and a sampling method by gold-platinum alloy amalgamation. However, the sample for analyzing stable mercury isotopes is necessarily a liquid having a concentration of mercury in liquid sample essentially higher than 1.0 ng/ml to be accurately detected by MC-ICP-MS for the composition of stable mercury isotopes. At present, the liquid oxidation method has the short enrichment time for a natural gas with low mercury content, it is difficult to analyze the stable mercury isotopes based on the low mercury content in the absorption liquid. Meanwhile, the solid oxidation method and the amalgam method are not suitable for the analysis of stable mercury isotopes.

SUMMARY

It is an object of the present disclosure to provide a method for detecting mercury isotopes in natural gas.

The present disclosure provides the composition analysis for stable mercury isotopes in different types of natural gas, in which a separation-absorption-enrichment device for absorbing and enriching mercury by a primary three-stage cascading acidic potassium permanganate, can completely absorb mercury in natural gas, and a secondary mercury purification-enrichment-absorption device, can eliminate interference and influence of other substances in natural gas on the analysis on stable mercury isotopes. Through the analysis on mercury isotopes in different types of natural gas, a new method for identifying the natural gas genesis is established, which can quickly and accurately determine the natural gas genesis and source, and provide a new technology for oil and gas exploration.

Another object of the present disclosure is to provide a device for detecting mercury isotopes in natural gas.

Figure 1:
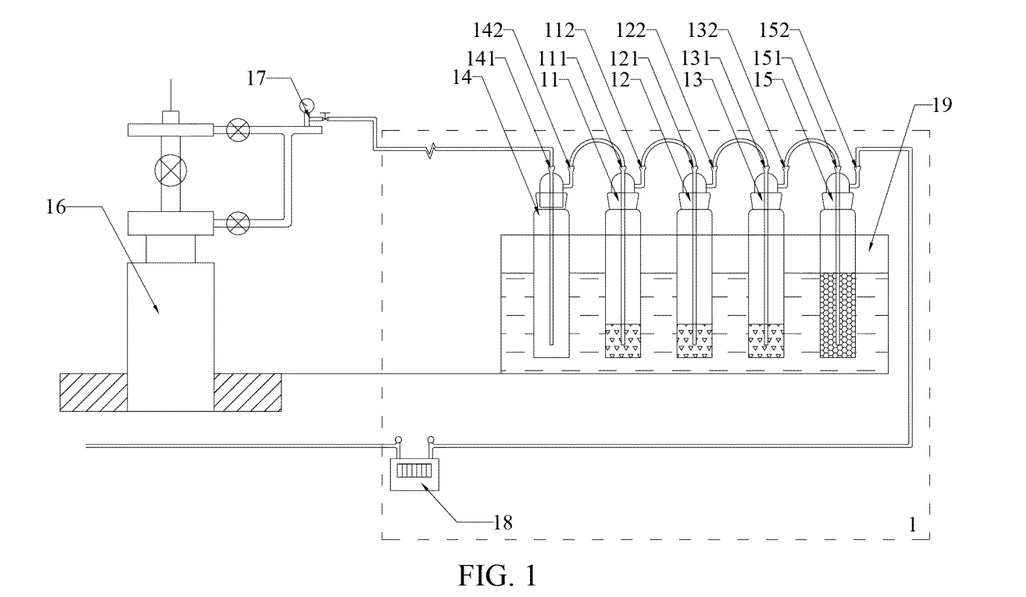
FIG. 1 is a schematic diagram of an enrichment-absorption system in Example 1.
Figure 2:
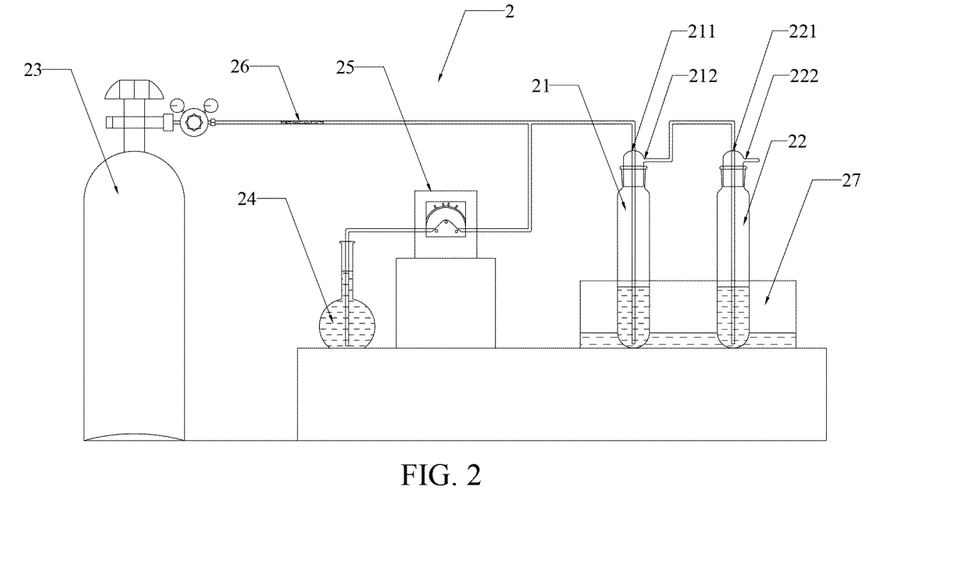
FIG. 2 is a schematic diagram of a secondary purification-enrichment system in Example 1.

To achieve the above object, in one aspect, the present disclosure provides a device for detecting mercury isotopes in natural gas, comprising an enrichment-absorption system 1 for mercury isotopes and a secondary purification-enrichment system 2, wherein the enrichment-absorption system 1 comprises an empty impact sampler 14, a first absorption bottle 11, a second absorption bottle 12, and a third absorption bottle 13 each containing an acidic potassium permanganate aqueous solution, and a silica-gel impact sampler 15 containing a silica gel, which are connected in series by pipe lines; the secondary purification-enrichment system 2 comprises a nitrogen-gas cylinder 23, a collection bottle 21 with potassium permanganate absorption liquid in which mercury isotope is absorbed, and a secondary enrichment-absorption bottle 22 containing an acidic potassium permanganate aqueous solution, which are connected in series by pipe lines, wherein the secondary purification-enrichment system 2 further comprises a stannous-chloride storage bottle 24, which is connected to a pipe line between the nitrogen-gas cylinder and the collection bottle 21 with potassium-permanganate absorption liquid via a peristaltic pump 25 and through a pipe line.

In accordance with some specific embodiments, in the device, each of the empty impact sampler 14, the first absorption bottle 11, the second absorption bottle 12, the third absorption bottle 13, the collection bottle 21 with potassium-permanganate absorption liquid and the secondary enrichment-absorption bottle 22 is a borosilicate glass bottle and is provided with a gas inlet and a gas outlet at the respective top thereof, wherein the gas inlet communicates with the inner space of the bottle through a glass tube which is provided with inside the bottle and extends to the lower part of the bottle.

In accordance with some specific embodiments, in the device, the empty impact sampler 14, the first absorption bottle 11, the second absorption bottle 12, the third absorption bottle 13, the silica-gel impact sampler 15, the collection bottle 21 with potassium permanganate absorption liquid and the secondary-enrichment absorption bottle 22 are connected by high-strength polytetrafluoroethylene tubes.

In accordance with some specific embodiments, in the device, each of the empty impact sampler 14, the first absorption bottle 11, the second absorption bottle 12, the third absorption bottle 13 and the silica-gel impact sampler 15 has a volume of 500 ml.

In accordance with some specific embodiments, in the device, the acidic potassium permanganate aqueous solution in the first absorption bottle 11, the second absorption bottle 12 and the third absorption bottle 13 are independently used in an amount filling to ⅕ to ⅓ of the height of the available volume in each absorption bottle.

In accordance with some specific embodiments, in the device, the silica gel in the silica-gel impact sampler 15 is used in the amount filling to ¼ to ¾, preferably ½, of the height of the available volume in the sampler.

In accordance with some specific embodiments, in the device, the acidic potassium permanganate solution in the secondary enrichment-absorption bottle 22 is used in an amount filling to ¼ to ¾, preferably ⅓, of the height of the available volume in the bottle.

In accordance with some specific embodiments, in the device, a first sink 19 is provided outside the empty impact sampler 14, the first absorption bottle 11, the second absorption bottle 12, the third absorption bottle 13 and the silica-gel impact sampler 15 so that the empty impact sampler 14, the first absorption bottle 11, the second absorption bottle 12, the third absorption bottle 13 and the silica-gel impact sampler 15 are disposed in the first sink 19.

In accordance with some specific embodiments, in the device, a second sink 27 is further provide outside the collection bottle 21 with potassium permanganate absorption liquid and the secondary enrichment-absorption bottle 22, so that the collection bottle 21 with potassium permanganate absorption liquid and the secondary enrichment-absorption bottle 22 are disposed in the second sink 27.

In accordance with some specific embodiments, in the device, in the enrichment-absorption system 1, the respective gas outlet of the impact sampler 14, the first absorption bottle 11, the second absorption bottle 12, the third absorption bottle 13 and the silica-gel impact sampler 15 is respectively connected to the gas inlet of the adjacent bottle via pipe lines, and the gas inlet 141 of the empty impact sampler 14 is connected to the natural gas well outlet 17 of the natural gas well 16; and in the secondary purification-enrichment system 2, the gas outlet of the nitrogen-gas cylinder 23 is connected to the gas inlet 211 of the collection bottle 21 with potassium permanganate absorption liquid, and the gas outlet 212 of the collection bottle 21 with potassium permanganate absorption liquid is connected to the gas inlet 221 of the secondary enrichment-absorption bottle 22.

In accordance with some specific embodiments, in the device, the enrichment-absorption system 1 further comprises a cumulative gas flow meter 18, which is connected via a pipe line to the gas outlet 152 of the silica-gel impact sampler 15.

In accordance with some specific embodiments, in the device, the secondary purification-enrichment system 2 further comprises a mercury-trapping gold tube 26 which is disposed on a pipe line connecting the nitrogen-gas cylinder 23 and the collection bottle 21 with potassium permanganate absorption liquid, and approximates to the gas outlet of the nitrogen-gas cylinder 23.

In accordance with some specific embodiments, the device further comprises a detector for detecting the total mercury content of the mercury enriched in the secondary enrichment-absorption bottle 22 and a detector for detecting the composition of stable isotopes of the mercury enriched in the secondary enrichment-absorption bottle 22.

In accordance with some specific embodiments, in the device, the detector for detecting the total mercury content of the mercury enriched in the secondary enrichment-absorption bottle 22 is a cold atomic fluorescence mercury detector, and the detector for detecting the composition of stable isotopes of the mercury enriched in the secondary enrichment-absorption bottle 22 is a multi-collector inductively-coupled plasma mass spectrometer.

In another aspect, the present disclosure provides a method for detecting mercury isotopes in natural gas, comprising the steps of:

(1) primary enrichment: subjecting natural gas to a three-stage cascading absorption with an acidic potassium permanganate aqueous solution, and collecting all of the acidic potassium permanganate aqueous solutions in which natural gas is absorbed in step (1);

(2) mercury purification and enrichment: reducing the mercury absorbed in the step (1) to mercury vapor with a stannous chloride solution, and then purifying and enriching the mercury vapor by using an acidic potassium permanganate aqueous solution;

(3) detecting the acidic potassium permanganate solution in which the mercury vapor is enriched in step (2) to determine the total mercury content therein;

(4) detecting the acidic potassium permanganate solution in which the mercury vapor is enriched in step (2) to determine the composition/content of stable mercury isotopes therein.

In accordance with some specific embodiments, the method for detecting mercury isotopes in natural gas is carried out by using the device for detecting mercury isotopes in natural gas.

In accordance with some specific embodiments, in the method, the natural gas in step (1) has a flow rate of 0.5 to 0.7 L/h.

In the present disclosure, a small amount of natural gas is released to the empty impact sampler at a flow rate is between 0.5 L/h and 0.7 L/h by adjusting the valve opening of the gas well. During sampling, it is noted that the potassium permanganate solution in the silica-gel impact sampler should be kept in a color of dark purple, so as to prevent potassium permanganate from being neutralized by reducing substances in natural gas and losing the ability to absorb and enrich mercury. The sampling process should be stopped immediately if the solution becomes colorless. After sampling, the sampling time shall be recorded in time, the natural gas flow shall be collected, and the samples shall be numbered and recovered.

In accordance with some specific embodiments, in the method, step (1) further comprises passing the natural gas firstly into the empty impact sampler 14 and then passing the natural gas out from the empty impact sampler into three cascading acidic-potassium-permanganate absorption bottles 11, 12, 13 to perform the three-stage cascading absorption, and passing the residual natural gas after absorption into a silica-gel impact sampler 15.

In accordance with some specific embodiments, in the method, collecting all of the acidic potassium permanganate solution in which natural gas is absorbed in the step (1) comprises transferring the acidic potassium permanganate solutions in which natural gas is absorbed in three acidic-potassium-permanganate absorption bottles into a collection bottle, washing off the brown spots on the acidic-potassium-permanganate absorption bottle with a 10 w/w % aqueous hydroxylamine hydrochloride solution until the brown spots are completely removed, and then combining the washed solution with the acidic potassium permanganate solution in the collection bottle.

In accordance with some specific embodiments, in the method, step (1) further comprises controlling the time for three-stage cascading absorption for natural gas in step (1), so that the collected acidic potassium permanganate solution has a mercury content of the equation to or greater than 1.0 ng/ml.

In accordance with some specific embodiments, in the method, step (1) further comprises a step of detecting the mercury content in the collected acidic potassium permanganate solution in which natural gas is absorbed, and adjusting the time for three-stage cascading absorption according to the measured mercury content, so that the collected acidic potassium permanganate solution has a mercury content of the equation to or greater than 1.0 ng/ml.

In accordance with some specific embodiments, in the method, step (1) comprises transferring, respectively, solutions of $KMnO_4$v/v+$H_2SO_4$w/v in three absorption bottles into a 1000 mL measuring cylinder, washing the few brown spots on the absorption bottles with 10% hydroxylamine hydrochloride solution as washing solution until the brown spots are completely removed, then pouring the washed solution back into the measuring cylinder, obtaining readout and transferring the washed solution into a cleaned borosilicate glass bottle, capping the bottle, numbering and recording. The bottle is light shielded by an aluminum foil paper, sealed with self-sealing bag, kept in refrigerator at low temperature to avoid mercury reduction and dissipation. On the same day, a portable Lumex RA-915M and its liquid attachments were used to preliminarily measure the mercury content in the absorption solution to adjust the next sampling time, so that the mercury content was higher than 1.0 ng/ml to meet the analysis requirement for mercury isotopes.

In accordance with some specific embodiments, in the method, the preliminary analysis for mercury in a natural-gas absorption liquid is performed by a RA-915M type portable mercury analyzer and its liquid attachments. In the analyzer, the liquid attachment is composed of two quartz tubes, wherein the outer tube is added with a small amount of distilled water and then added a small amount of stannous chloride solution, in which stannous chloride is used mainly to reduce the ionic mercury in the absorption liquid into the atomic mercury. Then the atomic mercury is carried out by a self-priming pump and sent to the main body of Lumex for analysis. The second quartz tube is charged with 30% sodium hydroxide solution that is used mainly to prevent the corrosion of the instrument by acidic gases volatilized from the $KMnO_4$+$H_2SO_4$ solution.

During the analysis, 5 ml of potassium permanganate solution enriched with mercury in natural gas is firstly taken, and 0.5 ml of 20% hydroxylamine hydrochloride solution is added to reduce the excessive potassium permanganate therein to colorless, then a 1 ml of solution is taken and the content of mercury enriched in the solution is preliminarily measured, finally an appropriate volume of solution for analysis is selected according to the analysis range in the standard curve, and the measurement result is recorded.

In step (1), since natural gas may have different composition and heat volatility due to the different types, the program settings for the pyrolysis temperature and the holding time of the front chamber are necessarily different depending on the different properties of natural gas. Typically, a sample with a mercury content of ppb level requires 7-8 hours for the pyrolysis/cracking pre-enrichment process.

If the sample has a lower mercury content, its amount for the pyrolysis/cracking pre-enrichment process can be increased.

In accordance with some specific embodiments, in the method, step (2) is the step of reducing the mercury absorbed in step (1) to mercury vapor with an aqueous stannous chloride solution having a concentration of 15 to 25 w/v %.

In accordance with some specific embodiments, in the method, the acidic potassium permanganate aqueous solutions used in step (1) have an acid concentration of 10%, and a potassium permanganate concentration of 4% each independently.

In accordance with some specific embodiments according to the present invention, in the method, the acidic potassium permanganate aqueous solutions used in step (2) have an acid concentration of 10%, and a potassium permanganate concentration of 1% each independently.

In accordance with some specific embodiments, in the method, the acid in the acidic potassium permanganate aqueous solutions used in step (1) and step (2) is sulfuric acid, respectively.

In accordance with some specific embodiments, in the method, step (2) comprises pumping a stannous chloride solution into the acidic potassium permanganate solution in which a natural gas is absorbed, collected in step (1), using nitrogen gas as a carry gas, to reduce mercury for mercury vapor, and feeding the mercury vapor into the acidic potassium permanganate aqueous solution with nitrogen gas to purify and enrich the mercury vapor.

In accordance with some specific embodiments, in the method, the nitrogen gas used as a carry gas in step (2) is subjected to mercury trapping treatment prior to contact the acidic potassium permanganate solution collected in step (1).

In accordance with some specific embodiments, in the method, step (2) comprises adding slowly a stannous chloride solution, by a peristaltic pump 25, into the acidic potassium permanganate solution in which a natural gas is absorbed, collected in step (1), using nitrogen gas as a carry gas, reducing mercury in the pre-enrichment absorption liquid by stannous chloride to mercury vapor, which is then purified and enriched by the acidic potassium permanganate aqueous solution (10% $H_2SO_4$+1% $KMnO_4$) in the secondary enrichment-absorption bottle 22 to eliminate impurity interference in the analysis for stable mercury isotopes.

In accordance with some specific embodiments, in the method, step (3) is the step of detecting the acidic potassium permanganate solution in which the mercury vapor is enriched in step (2) with a cold atomic fluorescence mercury detector; and step (4) is the step of detecting the acidic potassium permanganate solution in which the mercury vapor is enriched in step (2) with a multi-collector inductively coupled plasma mass spectrometer.

In accordance with some specific embodiments, in the method, step (3) is the step of analyzing the total mercury content in a secondary purified-enriched sample with a cold atomic fluorescence Brooks model III mercury detector.

In order to ensure the accuracy of sample analysis, the main reagent for mercury enrichment and absorption must be a chemical reagent with low mercury blank, when a cold atomic fluorescence Brooks model III mercury detector was used to analyze the total mercury content in the secondary purified-enriched sample.

In accordance with some specific embodiments, in the method, step (4) is the step of detecting the acidic potassium permanganate solution in which the mercury vapor is enriched in step (2) with a Neptune-Plus II multi-collector inductively coupled plasma mass spectrometer.

In accordance with some specific embodiments, in the method, prior to the detection of the acidic potassium permanganate solution in which the mercury vapor is enriched in step (2) with a multi-collector inductively coupled plasma mass spectrometer, it is necessary to dilute the samples to 1.0 µg/L, 1.5 µg/L, 2.0 µg/L respectively, according to the total mercury concentration in the samples.

All samples are held or diluted to a volume greater than 20 ml (for 2 analyses). Prior to analysis, 1 mL of hydroxylamine hydrochloride solution with a mass concentration of 25% is added to the sample to reduce excessive potassium permanganate, after that each of solutions to be measured is filtered to new 45 ml centrifuge tubes by a disposable syringe and a microporous filter membrane (PVDF, D33 mm, 0.45 µm), and all samples are stored from light with an aluminum foil paper.

In accordance with some specific embodiments, in the method, the detection of total mercury content in step (3) is carried out by a Brooks model III cold atomic fluorescence mercury detector manufactured by Brooksrand Inc, USA with a detection limit of 0.1 pg, using an analysis method detailed in US EPA Method 1631. Prior to the analysis, it is necessary to add the sample to be measured to a bubble bottle, while an appropriate amount of hydroxylamine hydrochloride ($NH_2OH.HCl$) is used to reduce the excessive $KMnO_4$. The mercury is reduced to atomic mercury ($Hg^0$) by $SnCl_2$ in the bubble bottle, and $Hg^0$ is purged and trapped on a gold-plated mercury-trapping tube by purging high-purity $N_2$ through a purge-trapping system. After that, the mercury-trapping tube is heated at 450° C. for desorption, releasing the pre-enriched mercury. The mercury vapor is carried into a mercury detector by introducing high-purity Ar, and is irradiated by a resonance radiation light of 253.7 nm emitted by a mercury lamp in the instrument. The mercury atom radiates fluorescence, and the light signal is converted into a peak area, from which the mercury content is then calculated.

In accordance with some specific embodiments, in the method, the detection for mercury isotope composition/content in step (4) is carried out by a Nu plasma type multi-collector inductively coupled plasma mass spectrometer manufactured by Nu Instruments, UK, which is a dual-focus magnetic mass spectrometer. In the instrument, a continuous-flow feeding system is used, and the sample is reduced by a $SnCl_2$ solution to produce $Hg^0$ gas which is introduced into a plasma source, and the mass discrimination correction of the instrument is done with Tl ions produced by an Apex-Q atomizer (CETAC Technologies, Omaha, USA). The entire feeding process is performed by a compact peristaltic pump (Gilson Corp., USA) at a feeding flow rate of 0.75 ml/min. The receiving system of the instrument has 12 fixed Faraday cups and 3 ion receivers. Among those, seven Faraday Cups are used for Hg Isotopes detection. Ar gas with high purity is used as carrier gases for feeding and plasma in the experiment. In order to ensure the accuracy of mercury isotope detection, the mercury concentration in the sample shall be maintained between 0.5 to 2 µg/l. The isotope composition is expressed in 1000 nα with respect to the standard (NIST SRM 3133).

In accordance with some specific embodiments, the method further comprises a step (5) of: comparing and analyzing the composition information for the mercury isotopes in mass fractionation and mass-independent fractionation in different types of natural gas based on the detection results in steps (3) and (4), establishing the mercury information characteristics in mass fractionation and mass-independent fractionation in different types of natural gas, and establishing an identification parameter system for natural gas genesis, evaluating the favorable exploration area and providing basis for oil-gas exploration.

In accordance with some specific embodiments, in the method, in step (5), the information for different types of natural gas is compared and analyzed, and the value range and the critical parameters regarding the mercury isotope ratio are established by analyzing the mercury isotopes in natural gas from different deposit environment sources, so that the mercury information characteristics for the mass fractionation and mass-independent fractionation in different types of natural gas are summarized. The source of natural gas can be determined by rapid mercury isotope analysis using natural gas obtained from a newly drilled well, so as to guide natural gas exploration deployment.

In accordance with some specific embodiments, in the method, the natural gas is originating from natural gas sample from a normal well in the gas field, including natural gas of different genetic types and different region, as well as natural gas of different properties, such as dry gas, wet gas, condensate gas, oil associated gas, etc.

In accordance with some specific embodiments, in the method, all glassware (absorption bottles and impact samplers) in step (1) are washed with 15% $HNO_3$ solution and ultrapure water before each use. Prior to sample pre-enrichment, the rear chamber needs to be heated to 1100° C. and be held until the end of the experiment. The air mercury absorption system and the mercury enrichment system are installed, the corresponding solution or reagent is added into the impact samplers, and connected to the quartz inner tube in the tube furnace, and finally the vacuum pump is connected. The air tightness of the system is checked by connecting cumulative flow meters in front of the air mercury absorption system and in front of the vacuum diaphragm pump, respectively, before starting the experiment.

In summary, the present disclosure provides a method for detecting mercury isotopes in natural gas and a device therefor. The method according to the present disclosure has the following advantages:

The present disclosure provides the composition analysis for stable mercury isotopes in different types of natural gas, in which a separation-absorption-enrichment device for absorbing and enriching mercury by a primary three-stage cascading acidic potassium permanganate, which can completely absorb mercury in natural gas, and a secondary mercury purification-enrichment-absorption device, can eliminate interference and influence of other substances in natural gas on the analysis on stable mercury isotopes. Through the analysis on mercury isotopes in different types of natural gas, a new method for identifying the natural gas genesis is established, can quickly and accurately determine the natural gas genesis and source, and provide a new technology for oil and gas exploration.

DETAILED DESCRIPTION

In the following, a detailed description is provided for the implementation and beneficial effects of the present disclosure by way of specific examples, which are intended to help a better understanding for the essence and features of the present disclosure and are not intended to limit the implementable scope of the present disclosure.

Example 1

A device for detecting mercury isotopes in natural gas, comprising an enrichment-absorption system 1 and a secondary purification-enrichment system 2 for mercury isotopes. As shown in FIG. 1, the enrichment-absorption system 1 comprises an empty impact sampler 14, a first absorption bottle 11, a second absorption bottle 12, a third absorption bottle 13 each containing an acidic potassium permanganate aqueous solution, and a silica-gel impact sampler 15 containing a silica gel, which are connected in series by pipe lines; each of the empty impact sampler 14, the first absorption bottle 11, the second absorption bottle 12, the third absorption bottle 13, the collection bottle 21 with potassium-permanganate absorption liquid and the secondary enrichment-absorption bottle 22 is a borosilicate glass bottle and is provided with a gas inlet and a gas outlet at the respective top thereof, wherein the gas inlet communicates with the inner space of the bottle through a glass tube which is provided inside the bottle and extends to the lower part of the bottle. The respective gas outlet of the impact sampler 14, the first absorption bottle 11, the second absorption bottle 12, the third absorption bottle 13 and the silica-gel impact sampler 15 is respectively connected to the gas inlet of the adjacent bottle via pipe lines, and the gas inlet 141 of the empty impact sampler 14 is connected to the natural gas well outlet 17 of the natural gas well 16; the enrichment-absorption system 1 further comprises a cumulative gas flow meter 18, which is connected via a pipe line to the gas outlet 152 of the silica-gel impact sampler 15.

As shown in FIG. 2, the secondary purification-enrichment system 2 comprises a nitrogen-gas cylinder 23, a collection bottle 21 with potassium permanganate absorption liquid in which mercury isotope is absorbed, and a secondary enrichment-absorption bottle 22 containing an acidic potassium permanganate aqueous solution, which are connected in series by pipe lines, wherein the secondary purification-enrichment system 2 further comprises a stannous-chloride storage bottle 24, which is connected to a pipe line between the nitrogen-gas cylinder and the collection bottle 21 with potassium-permanganate absorption liquid via a peristaltic pump 25 and through a pipe line. The gas outlet of the nitrogen-gas cylinder 23 is connected to the gas inlet 211 of the collection bottle 21 with potassium permanganate absorption liquid, and the gas outlet 212 of the collection bottle 21 with potassium permanganate absorption liquid is connected to the gas inlet 221 of the secondary enrichment-absorption bottle 22. A mercury-trapping gold tube 26 is disposed on a pipe line connecting the nitrogen-gas cylinder 23 and the collection bottle 21 with potassium permanganate absorption liquid, and approximates to the gas outlet of the nitrogen-gas cylinder 23.

The device further comprises a cold atomic fluorescence Brooks model III mercury detector for detecting the total mercury content of the mercury enriched in the secondary enrichment-absorption bottle 22, and a Neptune-Plus II multi-collector inductively-coupled plasma mass spectrometer for detecting the composition of stable isotopes of the mercury enriched in the secondary enrichment-absorption bottle 22.

The mercury isotopes in natural gas is detected by the device for detecting mercury isotopes in natural gas in this Example, which comprises the steps of:

(1) primary enrichment: passing the natural gas firstly into the empty impact sampler 14 at a flow rate of 0.5 to 0.7 L/h and then passing the natural gas out from the empty impact sampler into three cascading acidic-potassium-permanganate absorption bottles 11, 12, 13 to perform the three-stage cascading absorption (each of the aqueous potassium permanganate solutions in the acidic-potassium-permanganate absorption bottle has an acid (which is sulfuric acid) concentration of 10%, and a potassium permanganate concentration of 4%), and passing the residual natural gas after absorption into a silica-gel impact sampler 15; transferring the acidic potassium permanganate solutions in which natural gas is absorbed in three acidic-potassium-permanganate absorption bottles into a collection bottle, washing off the brown spots on the acidic-potassium-permanganate absorption bottle with a 10 w/w % aqueous hydroxylamine hydrochloride solution until the brown spots are completely removed, and then combining the washed solution with the acidic potassium permanganate solution in the collection bottle; measuring the mercury content in the collected acidic potassium permanganate solutions in which natural gas is absorbed, and adjusting the time for three-stage cascading absorption according to the measured mercury content, so that the collected acidic potassium permanganate solution has a mercury content of equal to or greater than 1.0 ng/ml;

The preliminary analysis for mercury in the acidic potassium permanganate solutions in which natural gas is absorbed is performed by a RA-915M type portable mercury analyzer and its liquid attachments. In the analyzer, the liquid attachment is composed of two quartz tubes, wherein the outer tube is added with a small amount of distilled water and then added with a small amount of stannous chloride solution, in which stannous chloride is used mainly to reduce the ionic mercury in the absorption liquid into the atomic mercury. Then the atomic mercury is carried out by a self-priming pump and sent to the main body of Lumex for analysis. The second quartz tube is charged with 30% sodium hydroxide solution that is used mainly to prevent the corrosion of the instrument by acidic gases volatilized from the $KMnO_4+H_2SO_4$ solution. During analysis, 5 ml of potassium permanganate solution enriched with mercury in natural gas is firstly taken, and 0.5 ml of 20% hydroxylamine hydrochloride solution is added to reduce the excessive potassium permanganate therein to colorless, then a 1 ml of solution is taken and the content of mercury enriched in the solution is preliminarily measured, finally an appropriate volume of solution for analysis is selected according to the analysis range in the standard curve, and the measurement result is recorded.

(2) mercury purification and enrichment: pumping a stannous chloride solution (having a concentration of 20 w/v %) into the acidic potassium permanganate solutions in which a natural gas is absorbed (having an acid (which is sulfuric acid) concentration of 10%, and a potassium permanganate concentration of potassium permanganate of 1% each independently), collected in step (1), using nitrogen gas as a carry gas, to reduce mercury to mercury vapor, and feeding the mercury vapor into the acidic potassium permanganate aqueous solution with nitrogen gas to purify and enrich the mercury vapor.

(3) detecting the acidic potassium permanganate solution in which the mercury vapor is enriched in step (2) by a cold atomic fluorescence Brooks model III mercury detector to determine the total mercury content therein;

The detector has a detection limit of 0.1 pg, and is performed by an analysis method detailed in US EPA Method 1631. Prior to the analysis, it is necessary to add the sample to be measured to a bubble bottle, while an appropriate amount of hydroxylamine hydrochloride (NH$_2$OH.HCl) is used to reduce the excessive KMNO$_4$. The mercury is reduced to atomic mercury (Hg$^0$) by SnCl$_2$ in the bubble bottle, and Hg$^0$ is purged and trapped on a gold-plated mercury-trapping tube by purging high-purity N$_2$ through a purge-trapping system. After that, the mercury-trapping tube is heated at 450° C. for desorption, releasing the pre-enriched mercury. The mercury vapor is carried into a mercury detector by introducing high-purity Ar, and is irradiated by a resonance radiation light of 253.7 nm emitted by a mercury lamp in the instrument. The mercury atom radiates fluorescence, and the light signal is converted into a peak area, from which the mercury content is then calculated.

(4) detecting the acidic potassium permanganate solution in which the mercury vapor is enriched in step (2) by a Neptune-Plus II multi-collector inductively coupled plasma mass spectrometer to determine the composition/content of stable mercury isotopes therein.

The Nu plasma type multi-collector inductively coupled plasma mass spectrometer is a dual-focus magnetic mass spectrometer. In the instrument, a continuous-flow feeding system is used, and the sample is reduced by a SnCl$_2$ solution to produce Hg$^0$ gas which is introduced into a plasma source, and the mass discrimination correction of the instrument is done with Tl ions produced by an Apex-Q atomizer (CETAC Technologies, Omaha, USA). The entire feeding process is performed by a compact peristaltic pump (Gilson Corp., USA) at a feeding flow rate of 0.75 ml/min. The receiving system of the instrument has 12 fixed Faraday cups and 3 ion receivers. Among those, seven Faraday Cups are used for Hg Isotopes detection. Ar gas with high purity is used as carrier gases for feeding and plasma in the experiment. In order to ensure the accuracy of mercury isotope detection, the mercury concentration in the sample shall be maintained between 0.5 to 2 µg/l. The isotope composition is expressed in 1000l nα with respect to the standard (NIST SRM 3133).

Prior to the detection of the acidic potassium permanganate solution in which the mercury vapor is enriched in step (2) with a multi-collector inductively coupled plasma mass spectrometer, it is necessary to dilute the samples to 1.0 µg/L, 1.5 µg/L, 2.0 µg/L respectively, according to the total mercury concentration in the samples.

All samples are held or diluted to a volume greater than 20 ml (for 2 analyses). Prior to analysis, 1 mL of hydroxylamine hydrochloride solution with a mass concentration of 25% is added to the sample to reduce excessive potassium permanganate, after that each of solutions to be measured is filtered to new 45 ml centrifuge tubes by a disposable syringe and a microporous filter membrane (PVDF, D33 mm, 0.45 µm), and all samples are stored from light with an aluminum foil paper.

(5) comparing and analyzing information for different types in different types of natural gas based on the detection results in steps (3) and (4), and establishing the value range and the critical parameters regarding the mercury isotope ratio by analyzing the mercury isotopes in natural gas from different deposit environment sources, so that the mercury information characteristics for the mass fractionation and mass-independent fractionation in different types of natural are summarized. The source of natural gas can be determined by rapid mercury isotope analysis using natural gas obtained from a newly drilled well, so as to guide natural gas exploration deployment.

The results are as follows:

The analysis process is as follows:

The typical oil-type gas (oil-associated gas in Bohai Bay Basin oilfield) and coal-type gas (natural gas derived from Jurassic coal-measure source rocks in Tarim Basin) were collected separately, and were analyzed for mercury isotopes. The results are as follows.

The oil-associated gas from Bohai Bay Basin:

Well No. B101: $\delta^{202}$Hg value: −1.23 ‰±0.22‰, $\Delta^{199}$Hg value: 0.22 ‰±0.08‰;

Well No. H2: $\delta^{202}$Hg value: −0.12‰±0.16‰, $\Delta^{199}$Hg value: 0.16 ‰±0.05‰;

Well No. F9: $\delta^{202}$Hg value: −2.64 ‰±0.13‰, $\Delta^{199}$Hg value: 0.24 ‰±0.02‰;

The pure natural gas from Kucha coal-measure formation in Tarim Basin:

Well No. KL206: $\delta^{202}$Hg value: −5.17 ‰±0.12‰, $\Delta^{199}$Hg value: −0.21 ‰±0.08‰;

Well No. KS201: $\delta^{202}$Hg value: −3.69 ‰±0.32‰, $\Delta^{199}$Hg value: −0.16 ‰±0.04‰;

Well No. BZ102: $\delta^{202}$Hg value: −4.23 ‰±0.09‰, $\Delta^{199}$Hg value: −0.06 ‰±0.03‰;

The analysis results are in good agreement with the natural gas types. Therefore, a $\delta^{202}$Hg value of −3‰ and $\Delta^{199}$Hg value of 0‰ for natural gas may be used as indices to distinguish oil-type and coal-type gas. If the value is respectively larger than the index, the natural gas is an oil-type gas, conversely, it is a coal-type gas.

What is claimed is:

1. A device for detecting mercury isotopes in natural gas, comprising an enrichment-absorption system and a secondary purification-enrichment system for mercury isotopes, wherein:

the enrichment-absorption system comprises an empty impact sampler, a first absorption bottle, a second absorption bottle, and a third absorption bottle each containing an acidic potassium permanganate aqueous solution, and a silica-gel impact sampler containing a silica gel, which are connected in series by pipe lines;

the secondary purification-enrichment system comprises a nitrogen-gas cylinder, a collection bottle with potassium permanganate absorption liquid in which mercury isotope is absorbed, and a secondary enrichment-absorption bottle containing an acidic potassium permanganate aqueous solution, which are connected in series by pipe lines, wherein the secondary purification-enrichment system further comprises a stannous-chloride storage bottle, which is connected to a pipe line between the nitrogen-gas cylinder and the collection bottle with potassium-permanganate absorption liquid via a peristaltic pump and through a pipe line.

2. The device according to claim 1, wherein each of the empty impact sampler, the first absorption bottle, the second absorption bottle, the third absorption bottle, the silica-gel impact sampler, the collection bottle with potassium-permanganate absorption liquid and the secondary enrichment-absorption bottle is a borosilicate glass bottle and is provided with a gas inlet and a gas outlet at a respective top thereof, wherein the gas inlet communicates with an inner space of the bottle through a glass tube which is provided inside the bottle and extends to a lower part of the bottle.

3. The device according to claim 2, wherein in the enrichment-absorption system, the respective gas outlet of the empty impact sampler, the first absorption bottle, the second absorption bottle, the third absorption bottle and the silica-gel impact sampler is respectively connected to the gas inlet of the adjacent bottle via pipe lines, and the gas inlet of the empty impact sampler is connected to a natural gas well outlet of a natural gas well; and in the secondary purification-enrichment system, a gas outlet of a nitrogen-gas cylinder is connected to the gas inlet of the collection bottle with potassium permanganate absorption liquid, and the gas outlet of the collection bottle with potassium permanganate absorption liquid is connected to the gas inlet of the secondary enrichment-absorption bottle.

4. The device according to claim 1, wherein the enrichment-absorption system further comprises a cumulative gas flow meter, which is connected via a pipe line to a gas outlet of the silica-gel impact sampler.

5. The device according to claim 1, wherein the secondary purification-enrichment system further comprises a mercury-trapping gold tube which is disposed on a pipe line connecting the nitrogen-gas cylinder and the collection bottle with potassium permanganate absorption liquid, and approximates to a gas outlet of the nitrogen-gas cylinder.

6. The device according to claim 1, further comprising a detector for detecting a total mercury content of mercury enriched in the secondary enrichment-absorption bottle and a detector for detecting a composition of stable isotopes of the mercury enriched in the secondary enrichment-absorption bottle.

7. The device according to claim 6, wherein the detector for detecting the total mercury content of the mercury enriched in the secondary enrichment-absorption bottle is a cold atomic fluorescence mercury detector, and the detector for detecting the composition of stable isotopes of the mercury enriched in the secondary enrichment-absorption bottle is a multi-collector inductively-coupled plasma mass spectrometer.

8. A method for detecting mercury isotopes in natural gas, comprising the steps of:
 (1) primary enrichment: passing natural gas firstly into an empty impact sampler and then passing the natural gas out from the empty impact sampler into three cascading acidic-potassium-permanganate absorption bottles, each containing an acidic potassium permanganate aqueous solution, to perform a three-stage cascading absorption, and passing residual natural gas after absorption into a silica-gel impact sampler, and collecting all of the acidic potassium permanganate aqueous solutions in which natural gas is absorbed in step (1);
 (2) mercury purification and enrichment: pumping a stannous chloride solution into the acidic potassium permanganate solutions in which a natural gas is absorbed, collected in step (1), using nitrogen gas as a carry gas, to reduce mercury to mercury vapor, and feeding the mercury vapor into an acidic potassium permanganate aqueous solution with nitrogen gas to purify and enrich the mercury vapor;
 (3) detecting the acidic potassium permanganate solution in which the mercury vapor is enriched in step (2) to determine a total mercury content therein; and
 (4) detecting the acidic potassium permanganate solution in which the mercury vapor is enriched in step (2) to determine a composition/content of stable mercury isotopes therein.

9. The method according to claim 8, wherein the natural gas in step (1) has a flow rate of 0.5 to 0.7 L/h.

10. The method according to claim 8, wherein step (1) further comprises controlling time for the three-stage cascading absorption for natural gas in step (1), so that the collected acidic potassium permanganate solutions have a mercury content of equal to or greater than 1.0 ng/ml.

11. The method of claim 8, wherein step (2) is the step of reducing mercury absorbed in step (1) to mercury vapor with an aqueous stannous chloride solution having a concentration of 15 to 25 w/v %.

12. The method according to claim 8, wherein the acidic potassium permanganate aqueous solutions used in step (1) have an acid concentration of 10%, and a potassium permanganate concentration of 4% each independently; and the acidic potassium permanganate aqueous solution used in step (2) has an acid concentration of 10%, and a potassium permanganate concentration of 1%.

13. The method according to claim 8, wherein the acid in the acidic potassium permanganate aqueous solutions used in step (1) and step (2) is sulfuric acid, respectively.

14. The method according to claim 8, wherein the nitrogen gas used as a carry gas in step (2) is subjected to mercury trapping treatment prior to contacting the acidic potassium permanganate solutions collected in step (1).

15. The method according to claim 8, wherein step (3) is the step of detecting the acidic potassium permanganate solution in which the mercury vapor is enriched in step (2) with a cold atomic fluorescence mercury detector; and step (4) is the step of detecting the acidic potassium permanganate solution in which the mercury vapor is enriched in step (2) with a multi-collector inductively coupled plasma mass spectrometer.

16. The method according to claim 8, further comprising a step (5) of: comparing and analyzing composition information for the mercury isotopes in mass fractionation and mass-independent fractionation in different types of natural gas based on detection results in steps (3) and (4), establishing mercury information characteristics in mass fractionation and mass-independent fractionation in different types of natural gas, and establishing an identification parameter system for natural gas genesis, evaluating favorable exploration area and providing basis for oil-gas exploration.

17. The method according to claim 8, which performs the detection by a device for detecting mercury isotopes in natural gas comprising an enrichment-absorption system and a secondary purification-enrichment system for mercury isotopes, wherein:
 the enrichment-absorption system comprises an empty impact sampler, a first absorption bottle, a second absorption bottle, and a third absorption bottle each containing an acidic potassium permanganate aqueous solution, and a silica-gel impact sampler containing a silica gel, which are connected in series by pipe lines;
 the secondary purification-enrichment system comprises a nitrogen-gas cylinder, a collection bottle with potassium permanganate absorption liquid in which mercury isotope is absorbed, and a secondary enrichment-absorption bottle containing an acidic potassium permanganate aqueous solution, which are connected in series by pipe lines, wherein the secondary purification-enrichment system further comprises a stannous-chloride storage bottle, which is connected to a pipe line between the nitrogen-gas cylinder and the collection bottle with potassium-permanganate absorption liquid via a peristaltic pump and through a pipe line.

* * * * *